United States Patent
Peterson

(10) Patent No.: US 9,474,459 B2
(45) Date of Patent: Oct. 25, 2016

(54) ECG ELECTRODE AND LEADWIRE CONNECTION INTEGRITY DETECTION

(71) Applicant: General Electric Company, Schenectady, NY (US)

(72) Inventor: James R. Peterson, Wauwatosa, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 0 days.

(21) Appl. No.: 14/446,717

(22) Filed: Jul. 30, 2014

(65) Prior Publication Data

US 2016/0029915 A1   Feb. 4, 2016

(51) Int. Cl.
| | |
|---|---|
| *A61N 1/37* | (2006.01) |
| *A61N 1/39* | (2006.01) |
| *A61B 5/0424* | (2006.01) |
| *A61B 5/00* | (2006.01) |
| *A61B 5/0428* | (2006.01) |
| *A61B 5/0402* | (2006.01) |

(52) U.S. Cl.
CPC ........... *A61B 5/0424* (2013.01); *A61B 5/0428* (2013.01); *A61B 5/6843* (2013.01); *A61B 5/7221* (2013.01); *A61B 5/04028* (2013.01); *A61B 5/7257* (2013.01)

(58) Field of Classification Search
USPC .................... 600/508–509, 518; 607/7, 10
See application file for complete search history.

(56) References Cited

U.S. PATENT DOCUMENTS

| | | |
|---|---|---|
| 3,495,584 A | 2/1970 | Schwalm |
| 3,602,215 A | 8/1971 | Parnell |
| 6,516,218 B1 | 2/2003 | Cheng et al. |
| 2006/0015033 A1 | 1/2006 | Blakley et al. |
| 2006/0178706 A1* | 8/2006 | Lisogurski et al. ............ 607/10 |
| 2013/0331719 A1* | 12/2013 | Freeman et al. ............... 600/518 |
| 2014/0155947 A1* | 6/2014 | Kroll et al. ........................ 607/4 |

FOREIGN PATENT DOCUMENTS

| | | |
|---|---|---|
| EP | 0800787 A1 | 10/1997 |
| WO | 9215244 A1 | 9/1992 |
| WO | 2008056309 A2 | 5/2008 |

OTHER PUBLICATIONS

International Search Report and Written Opinion for PCT/US2015/039333, mail date Sep. 22, 2015, 10 pages.

* cited by examiner

*Primary Examiner* — Carl H Layno
*Assistant Examiner* — Jon Eric C Morales

(57) ABSTRACT

A system and method for ECG electrode and leadwire connection integrity detection are provided herein. The system includes a plurality of electrodes wherein a uniform spectral energy signal is to be injected into a subset of electrodes of the plurality of electrodes. The system also includes a computing device. The computing device includes a display, and the computing device is communicably coupled to the plurality of electrodes. The computing device is configured to acquire input signals from an electrode and determine a frequency response from the electrode based on the input signal from the electrode. The computing device is also configured to determine impairments in the electrode and leadwire connection using the frequency response.

19 Claims, 6 Drawing Sheets

400

100

300

400

ECG ELECTRODE AND LEADWIRE CONNECTION INTEGRITY DETECTION

BACKGROUND

An electrocardiograph is a device adapted to record the electrical activity of a patient's heart over time. The electrocardiograph includes one or more sensors or electrodes adapted for attachment to a patient and configured to sense electrical activity. The electrodes transmit electrical signals pertaining to the cardiac activity via a conductor such as a wire to a controller. The controller may generate a plot referred to as an electrocardiogram (ECG) based on the data from the electrodes.

In conventional ECG acquisition, one electrode is driven to a direct current (DC) potential such that the common-mode potential appearing at all of the other electrodes falls within the common-mode signal range of the ECG input amplifiers. The electrode may also be driven with a simple out-of-band tone in order to detect major lead failure conditions, such as an open circuit. However, this conventional ECG acquisition does not provide any additional information regarding the failure condition.

BRIEF DESCRIPTION

An embodiment relates to a system for ECG electrode and leadwire connection integrity. The system includes a plurality of electrodes wherein a signal with uniform spectral energy is to be injected into a subset of electrodes of the plurality of electrodes. The system also includes a computing device. The computing device includes a display, and the computing device is communicably coupled to the plurality of electrodes. The computing device is configured to acquire input signals from an electrode and determine a frequency response from the electrode based on the input signal from the electrode. The computing device is also configured to determine impairments in the electrode and leadwire connection using the frequency response.

Another embodiment relates to an ECG system. The ECG system includes a plurality of electrodes including a right leg electrode and a second electrode. The right leg electrode is to be driven by a chirp signal and to be releasably attached to a patient. An impedance between the second electrode and the right leg electrode is calculated, and the calculated impedance is used to determine a location of electrode connection impairment.

Still another embodiment relates to a method for ECG electrode and leadwire connection integrity detection. The method includes injecting a chirp signal into a neutral electrode, and measuring an impedance at a plurality of electrodes across a range of frequencies from the chirp signal. The method also includes calculating an impedance of pairs of electrodes of the plurality of electrodes from the measured impedance, and determining an impairment location based on the calculated impedance.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the present techniques.

To obtain an ECG plot, a set of electrodes are releasably attached to the body of a patient at various locations. The positioning of each electrode directly affects the quality and accuracy of the ECG. The electrodes are connected to electrode lead wires via an electrode head. The other end of the leadwires are connected to machinery that processes these electrical signals and produces data characteristic of the body function being monitored. In embodiments discussed herein, an impedance of the electrodes and lead wire connection to the patient is evaluated over a range of frequencies. A technical effect of at least one embodiment includes a chirp signal injected into an electrode. In some scenarios, the chirp signal has a uniform spectral energy content similar to an impulse so that the impedance of the electrodes and leadwire connection can be evaluated over a range of frequencies. In this manner, a more comprehensive assessment of the patient electrode and leadwire connection integrity is enabled in order to provide guidance to the caregiver on obtaining the best quality ECG recording.

Figure 1:
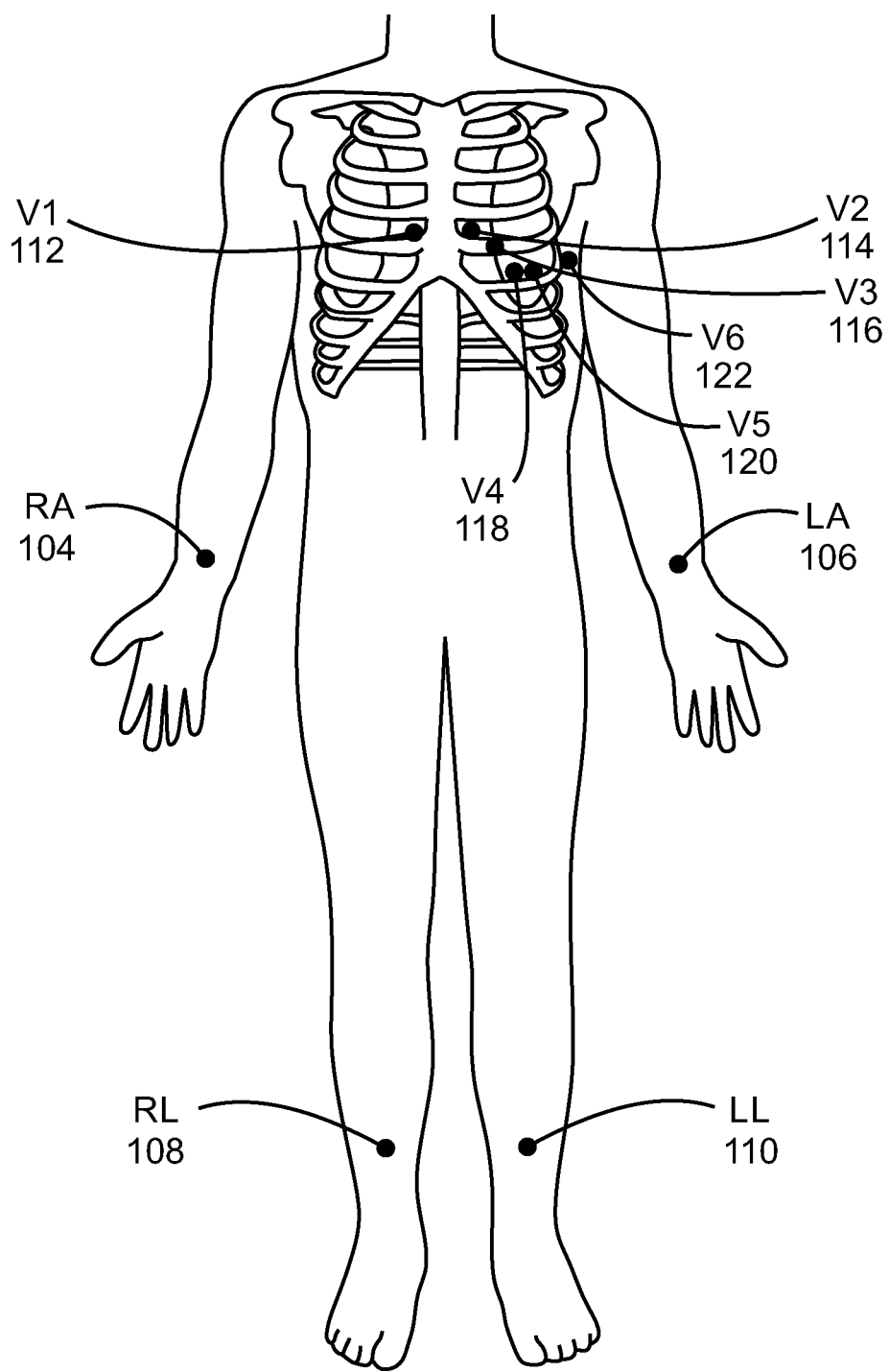
FIG. 1 is an exemplary illustration of a 12-lead ECG system in accordance with embodiments.

FIG. 1 is an exemplary illustration of a 12-lead ECG system 100 in accordance with embodiments. The 12-lead ECG system 100 provides twelve leads, pictures, or views of the heart through ten electrodes strategically placed on a patient 102. Although a 12-lead ECG system is described, the present techniques may be used with any number of leads in any diagnostic/monitoring system.

The 12-lead ECG system 100 in the example of FIG. 1 enables twelve views of electrical activity of the heart of patient 102 via the ten strategically placed electrodes. Four electrodes are limb electrodes which include a right arm (RA) electrode 104; a left arm (LA) electrode 106, a right leg (RL) electrode 108; and a left leg (LL) 110. Although electrodes RA 104 and LA 106 are shown as being attached to the patient's 102 wrists, they are may be applied at the patient's 102 shoulders. Similarly, although the electrodes RL 108 and LL 110 are shown as being attached to the patient's 102 ankles, they may be applied to the patient's 102 hips. In some cases, the RL 108 is considered a "dummy" or neutral electrode that functions as a ground.

The remaining six electrodes are applied to the chest of the patient 102. The six electrodes may be are placed at the 4th intercostal space right sternal edge (V1) 112, the 4th intercostal space left sternal edge (V2) 114, over the apex (5th ICS mid-clavicular line) (V4) 118, halfway between V2 and V4 (V3) 116, at the same level as V4 but on the anterior axillary line (V5) 120, and at the same level as V4 and V5 but on the mid-axillary line (V6) 118. The 12-leads or views of electrical activity can be acquired directly from the patient leads as well as derived using Einthoven's law. The electrodes V1 112, V2 114, V3 116, V4 118, V5 120, and V6 122 must be placed with a high degree of precision on the specific portions of the patient's 102 anatomy as illustrated in FIG. 1.

The process of attachment of the electrodes or leadwires to acquire ECG signals is prone to conditions that can result in poor quality signals. The magnitude of the electrode/leadwire impedance has a significant effect on the ability to obtain a quality ECG signal. According to the present techniques, the RL electrode is driven by a dynamic signal which can be controlled to output a low level chirp waveform imposed upon an average DC potential, thereby enabling a frequency response between each of the electrodes to be determined by taking a Fast Fourier Transform (FFT) of the input signal appearing at each electrode. The frequency response is then used to detect and classify impairments in the electrode/leadwire connection of each ECG signal lead. In this manner, the location of the connection impairment can be accurately determined.

The injection of the chirp signal results in improved feedback to clinician or patient in applying the electrodes, resulting in improved acquisition of ECG signals, especially in a patient initiated recording use case. Further, an average right leg (RL) bias voltage can be controlled in order to optimize the common-mode voltage appearing at each of the ECG lead input amplifiers. In some cases, controlling the average RL common-mode voltage is used to account for variations in electrode contact potential, reduce the chance of input amplifier saturation, and improve the common-mode rejection performance of the ECG input amplifiers.

In particular, the common-mode rejection performance can be improved by adjusting the chirp signal driving the RL so that it would center the input signals from the electrodes within a range of the input amplifiers, which would maximize the common-mode rejection and eliminate input saturation of the amplifiers. Accordingly, the DC potential that results from attaching an electrode to a patient can be adjusted up or down, eliminating the saturation in some cases and preserving the actual integrity of the signals being measured.

Figure 2A:
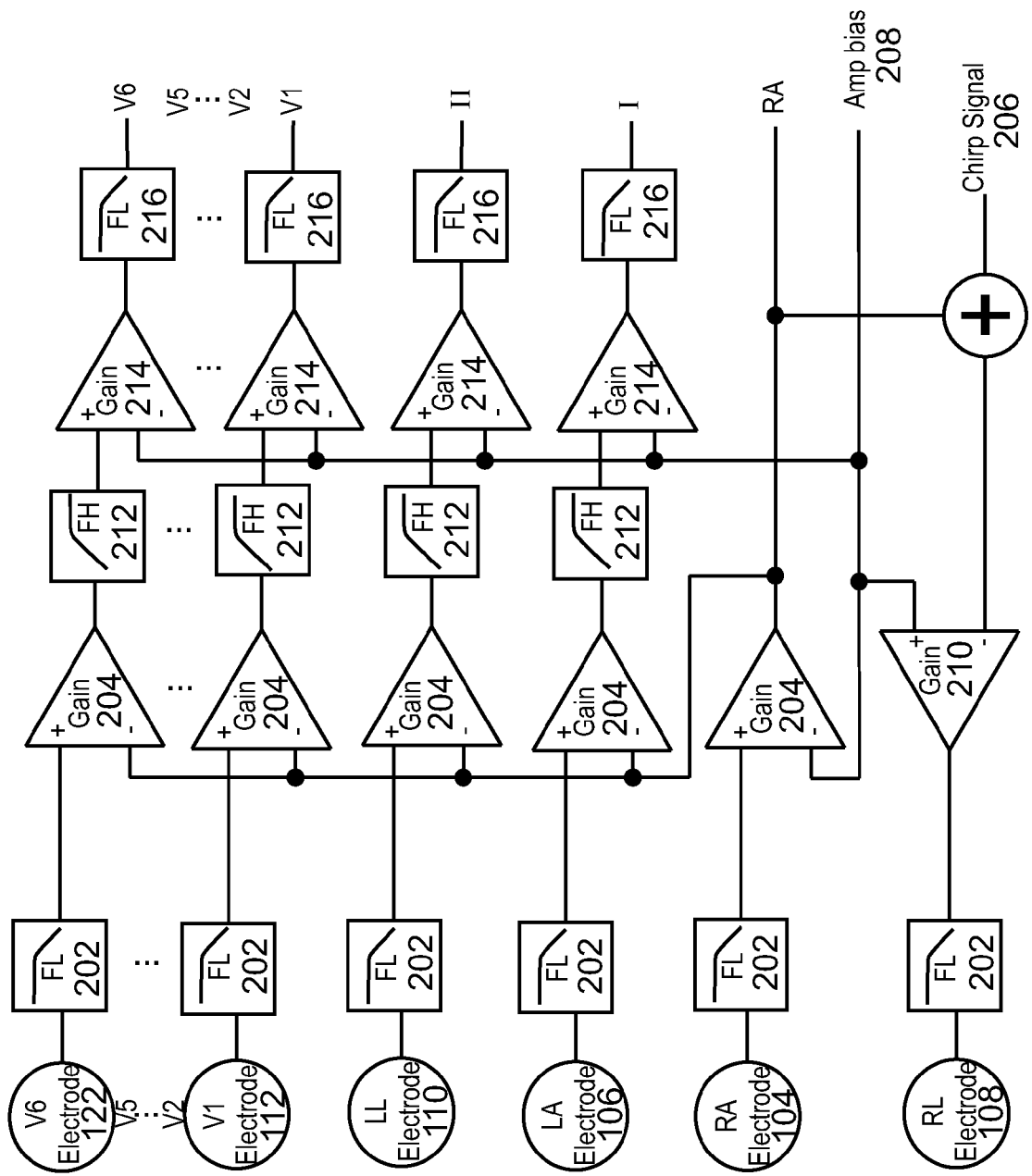
FIG. 2A is an illustration of a right arm reference electrode with common-mode feedback and chirp signal driving the right leg electrode, in accordance with embodiments.

FIG. 2A is an illustration of a right arm reference electrode with common-mode feedback and chirp signal driving the right leg electrode, in accordance with embodiments. As an example, chest electrodes V1 112 through V6 122 are illustrated. The signal from each electrode is passed through an RL drive 202 with a sufficiently high corner frequency. In some cases, the sufficiently high corner frequency is 40, 100, 150 Hz or higher. The RA common-mode feedback to the RL drive 202 can remove a power line noise on the signal obtained from the plurality of electrodes. After the RLD 202, the filtered signals from electrodes V1 112 through V6 122, LA 106, and RA 104 are sent through an amplifier 204. The amplifier 204 may be a differential amplifier used to enhance the difference between the electrode signals from the RA reference electrode.

The RL electrode 108 acts as an output and feeds signals back to the patient. As illustrated, a chirp signal 206 is summed with the filtered and amplified output of the RA 104 electrode. The amplifier 204 of the RA 104 electrode has as inputs the filtered signal from the RA 104 electrode and an amplifier bias 208. The summed chirp signal 208 and the amplifier bias 208 are input to an amplifier 210. The output of the amplifier 210 is filtered by a low pass filter 108 and then injected or driven on to the RL 108 electrode. This dynamic RL bias drive circuitry enables the impedance from each of the leadwires and electrodes RA 104, LA 106, LL 110, V1 112, V2 114, V3 116, V4 118, V5 120, and V6 122 to the RL 108 to be accurately measured over a predetermined frequency range. The measured impedance between the RL electrode and the other electrodes can then be used to calculate the impedance between any pair of electrodes or leadwires. This information can be used to notify the clinician or patient of which electrodes or leadwires require adjustment or replacement before recording the ECG signals.

As illustrated in FIG. 2A, a high pass filter 212 filters the amplified signals from the electrode V1 112 through V6 122, LL 110, and LA 106. Another amplifier 214 is applied to the electrode V1 112 through V6 122, LL 110, and LA 106. The amplifier 214 takes as input the respective signal from each electrode through the high pass filter 212 and the amplifier bias 208. The twice amplified signal is then sent through another low pass filter 216. After the low pass filter 216, each electrode V1 112 through V6 122, LL 110, and LA 106 can provide a lead or view of the heart to be displayed on a monitor or printout.

Accordingly, the ECG electrode and leadwire connection integrity detection is enabled by spectral analysis of the injected chirp signal 206. The chirp signal 206 has a uniform spectral energy content similar to an impulse so that the impedance of the electrode and leadwire connections to the patient can be evaluated over a range of frequencies, versus measuring the impedance at a single frequency, as is commonly done in current AC leadfail detection systems. By spreading the injected energy over a wide range of frequencies, a more accurate assessment of the patient interconnect impedance can be determined, including both the resistive and reactive (i.e., typically capacitive) components. This enables a more comprehensive assessment of the patient electrode and leadwire connection integrity in order to provide guidance to the caregiver on obtaining the best quality ECG recording.

In embodiments, the chirp signal is a low level chirp waveform imposed upon an average DC potential, enabling the frequency response between each of the electrodes to be determined by taking the Fast Fourier Transform (FFT) of the input signal appearing at each electrode. The frequency response is then used to detect and classify impairments in the electrode and leadwire connection of each ECG signal lead. This information can also be used to accurately determine the location of the connection impairment.

In embodiments, the present techniques are able to determine a poor electrode connection to a patient at low frequencies. A conventional ECG system can detect a good capacitive reactive impedance connection to the patient via a 250 Hertz (Hz) signal used to evaluate the impedance and frequency response of the electrodes at the single 250 Hz frequency. However, an electrode or leadwire connection to a patient can be a poor connection at lower frequencies while showing a good connection at a 250 Hz frequency. The present techniques can be used to detect the poor connection at the lower frequencies. Additionally, the present techniques can be used to determine a low frequency impairment resulting from an impedance that is higher than a particular threshold at an electrode or leadwire connection.

As illustrated in FIG. 2A, signals from each input electrode are measured with respect to the right arm, as the right arm signal serves as an input to an amplifier for the other electrodes. The amplifiers, such as the amplifiers 204, are to measure differential signals. However, there is a certain range of common mode voltages that the amplifiers can amplify. In accordance with the present techniques, the RL electrode 108 is used to apply a potential to the patient such that all the other amplifier inputs are biased correctly and the voltage present at the other electrode inputs is valid for the amplifiers that are actually attached to the patient at this point.

In some cases, a differential amplifier such as amplifier 204 can measure the difference between two voltages, and as long as the absolute or common-mode voltage is within a certain range the amplifier 204 can amplify the signals. For example, if the amplifier has its power supplied at −5 and +5 volts, it can amplify the different signals as long as the input voltages on each of the differential inputs are within the −5V to +5V range. If the differential inputs are outside of that range, the amplifier will not work correctly as a linear component. Accordingly, applying a potential to the right leg of the patient basically biases the amplifiers to ensure the differential inputs are within the correct range. Further, applying the chirp signal to the right leg gives a driven output that can generate more than a DC signal. The signals are biased and analyzed across a range of frequencies to detect a wider range of connection impairments when compared to a conventional ECG system.

Figure 2B:
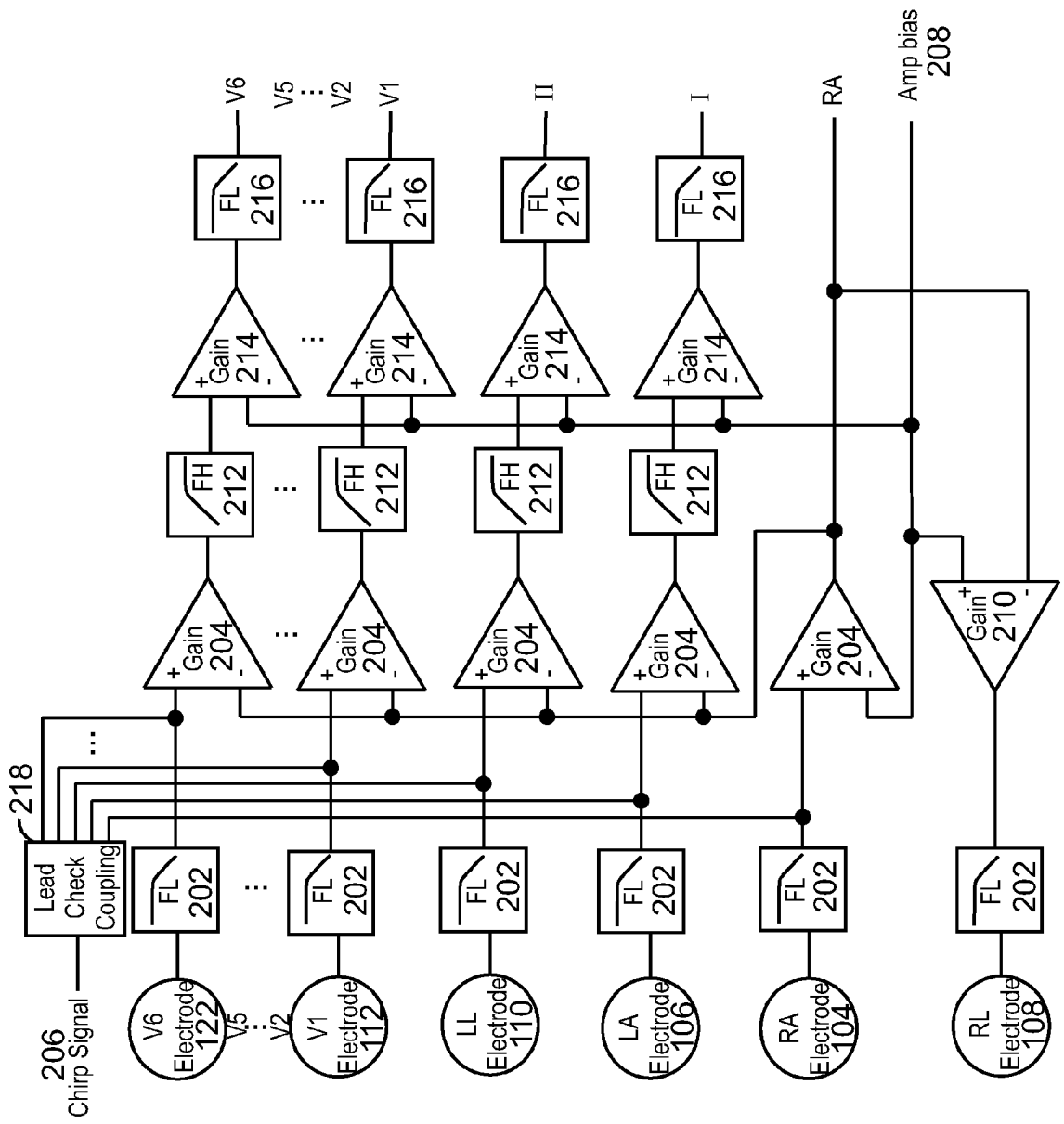
FIG. 2B is an illustration of electrodes and chirp signal driving left arm, right arm, and chest electrodes in accordance with embodiments.

FIG. 2B is an illustration of electrodes and chirp signal driving left arm, right arm, and chest electrodes in accordance with embodiments. As an example, chest electrodes V1 112 through V6 122 are illustrated. The signal from each electrode is passed through the RL drive 202 as described with respect to FIG. 2A. After the RL drive 202, the filtered signal is coupled with a chirp signal 206 that has passed through a lead check coupling 218. The signal then proceeds through an amplifier 204. The second input on the amplifier 204 is from the RA 104 electrode in order to bias and amplify the filtered signals.

FIG. 2B illustrates an alternative technique of injecting the chirp signal into each individual electrode input. The chirp signal is injected as a current source (i.e., high source impedance) so that the amplitude of the chip signal picked up on each electrode input will be a function of the impedance between that electrode and the RL electrode such that the higher the impedance, the large the chirp voltage will be that appears on that particular input.

Figure 3:
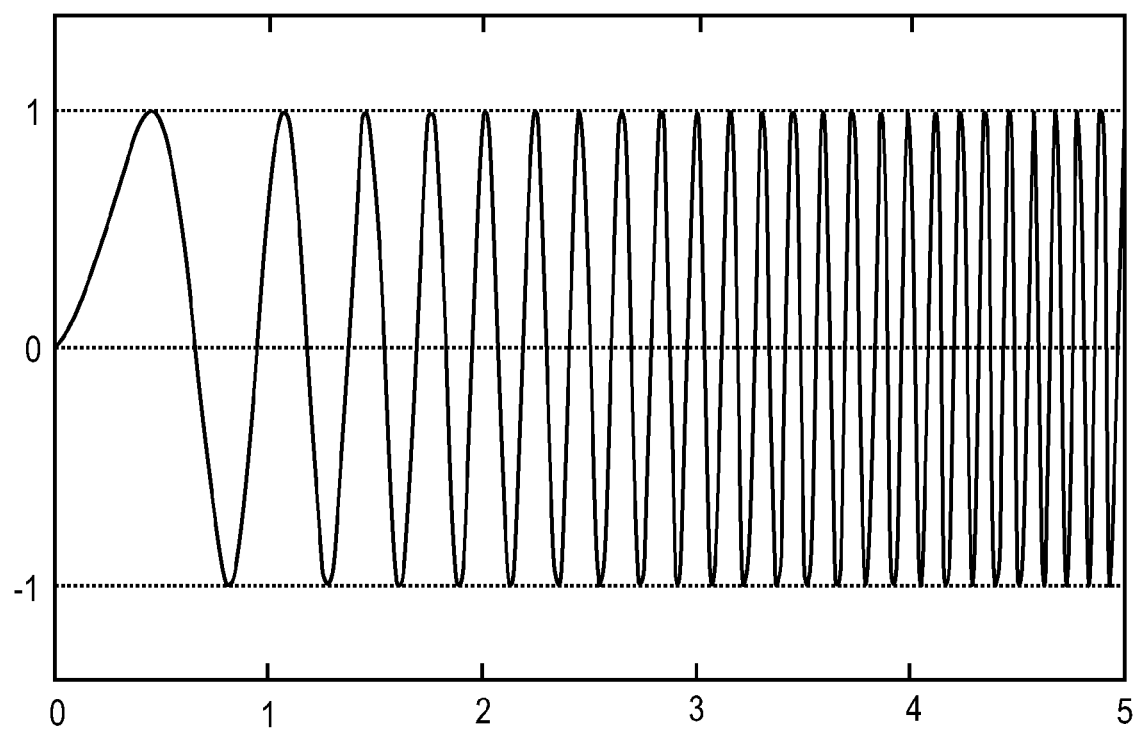
FIG. 3 is an example of a chirp signal according to embodiments.

FIG. 3 is an example of a chirp signal 300 according to embodiments. In some cases, the chirp signal 300 is a signal that has uniform spectral energy content. As illustrated, the chirp signal includes values throughout an entire frequency bandwidth (Hz) via a sinusoidal waveform of constant amplitude within particular time. In some embodiments, an impulse signal can be used instead of a chirp signal. Furthermore, other waveforms can be used by applying an inverse operation to arrive at a uniform spectral density over frequencies applicable to ECG monitoring.

Figure 4:
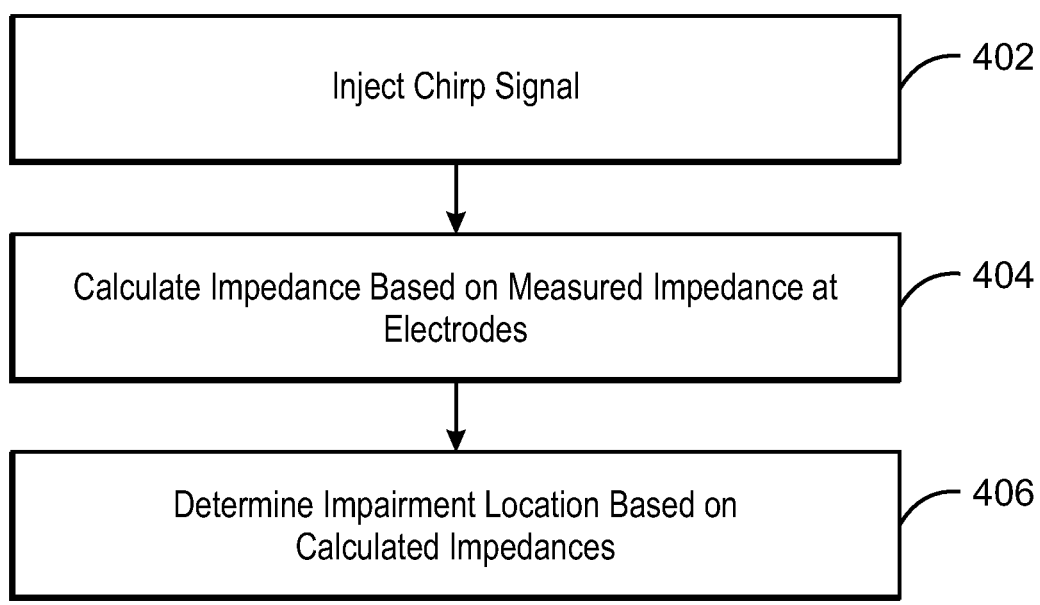
FIG. 4 is a process flow diagram of a method for determining electrode and leadwire connection integrity detection.

FIG. 4 is a process flow diagram of a method 400 for determining electrode and leadwire connection integrity detection. At block 402, a chirp signal is injected into a subset of a plurality of electrodes. In some embodiments, the subset is a neutral electrode, such as the RL electrode as illustrated in FIG. 2A. In other embodiments, the subset of the plurality of electrodes include the chest electrodes, LL electrode, LA electrode, and RA electrode as illustrated in FIG. 2B. At block 404, first impedance can measured at each electrode of the plurality of electrodes, and an impedance between pairs of electrodes is calculated based on the measure impedances. At block 406, an impairment location is determined based on the calculated impedances.

In some embodiments, the type of impairment can be classified depending on the frequency response and calculated impedance at the electrode or leadwire connection. When the impedances or frequency responses are outside of a pre-determined threshold, a connection impairment can be detected and classified. In particular, an electrode or leadwire failures at a lower frequency may indicate that the resistance of the connection to the patient is too high. A high resistance at the connection may be caused by a poor skin condition. In particular, the surface of the skin where the electrodes are attached may need to be upgraded, or foreign substances may need to be removed from the skin, such as lotion or oils. Upgrading the skin can include, but is not limited to, shaving hair or scrubbing the skin to enable a better skin to electrode connection.

A connection impairment can be detected prior to recording, displaying, or otherwise acquiring an ECG plot. In some cases, a connection impairment is included in a ECG preparation procedure. In some embodiments, the connection impairment may be determined during acquisition of ECG signals. In this manner, the electrode connection quality can be monitored throughout an ECG acquisition.

Figure 5:
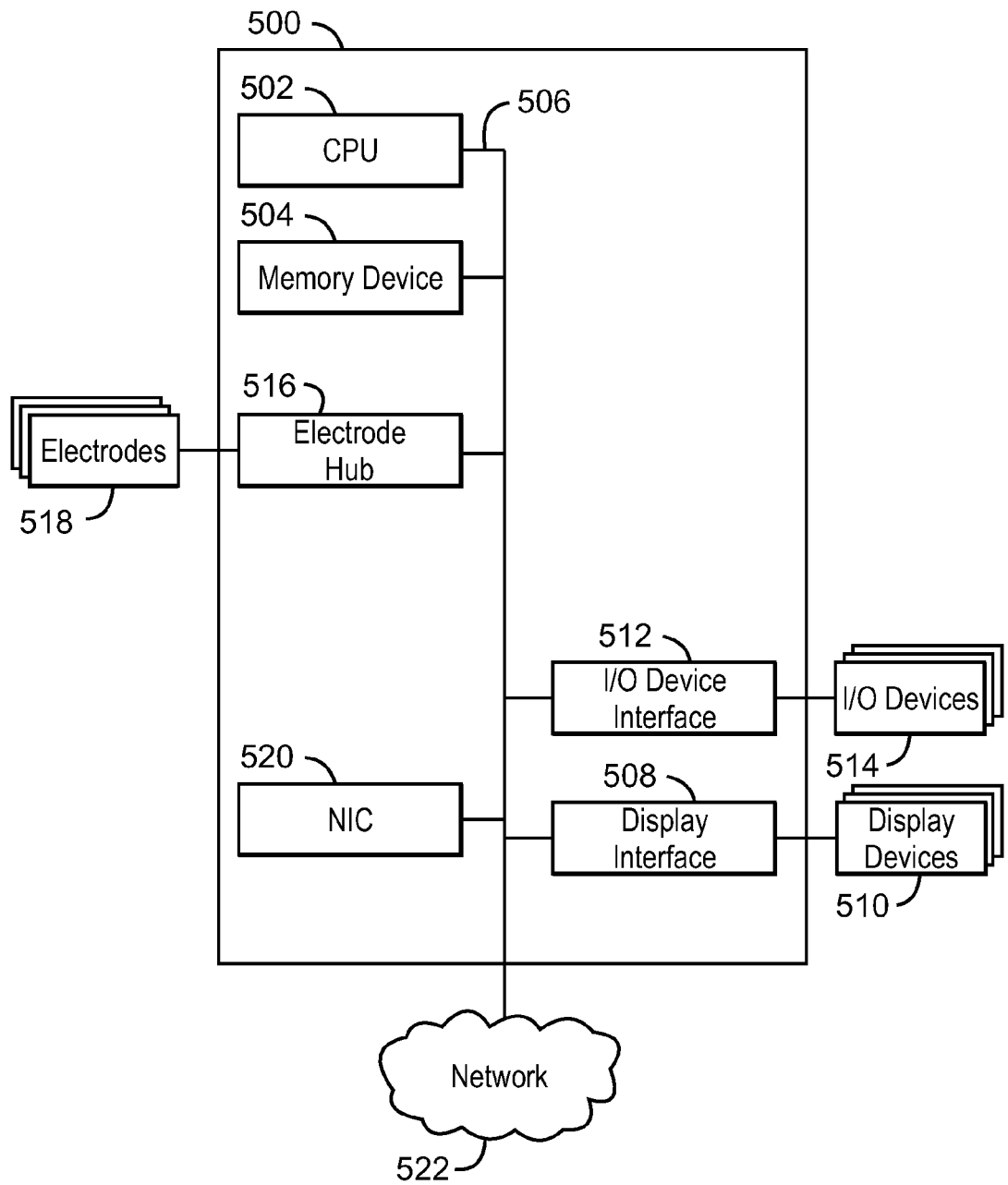
FIG. 5 is a block diagram of a patient monitoring device used in accordance with an embodiment.

FIG. 5 is a block diagram of a patient monitoring device 500 that may be used in accordance with an embodiment. The patient monitoring device 500 may be, for example, a electrocardiograph, a computing device, or any other patient monitoring device that measures physiological parameters of a patient. The patient monitoring device 500 may include a central processing unit (CPU) 502 that is configured to execute stored instructions, as well as a memory device 504 that stores instructions that are executable by the CPU 502. The CPU may be coupled to the memory device 504 by a bus 506. Additionally, the CPU 502 can be a single core processor, a multi-core processor, a computing cluster, or any number of other configurations. Furthermore, the patient monitoring device 500 may include more than one CPU 502. The memory device 504 can include random access memory (RAM), read only memory (ROM), flash memory, or any other suitable memory systems. For example, the memory device 504 may include dynamic random access memory (DRAM).

The CPU 502 may be linked through the bus 506 to a display interface 508 configured to connect the patient monitoring device 500 to a display device 510. The display device 510 may include a display screen that is a built-in component of the patient monitoring device 500. The display device 510 may also include a computer monitor, television, or projector, among others, that is externally connected to the patient monitoring device 500. In some cases, the display is used to output information on the status of a patient, including an ECG, connection impairments as described herein and various alerts.

The CPU 502 may also be connected through the bus 506 to an input/output (I/O) device interface 512 configured to connect the patient monitoring device 500 to one or more I/O devices 514. The I/O devices 514 may include, for example, a keyboard and a pointing device, wherein the pointing device may include a touchpad or a touchscreen, among others. The I/O devices 514 may be built-in components of the patient monitoring device 500, or may be devices that are externally connected to the patient monitoring device 500.

The computing device also includes a electrode hub 516. The electrode hub 516 may be coupled to a plurality of electrodes 518. In embodiments, the electrodes 518 form a 12-lead ECG system as described herein. In other embodiments, the electrodes 518 form a 15-lead ECG system. The patient monitoring device 500 may also include a network interface controller (NIC) 520 configured to connect the patient monitoring device 500 through the bus 506 to a network 522. The network 526 may be a wide area network (WAN), local area network (LAN), or the Internet, among others. In some cases, the network 526 is a patient monitoring network. Additionally, in some cases, the network is secure. The patient monitoring network can be used to measure and display physiological parameters, such as a patient's pulse rate and blood pressure.

The block diagram of FIG. 5 is not intended to indicate that the patient monitoring device 500 is to include all of the components shown in FIG. 5. Further, the patient monitoring device 500 may include any number of additional components not shown in FIG. 5, depending on the details of the specific implementation.

While embodiments are described herein with respect to cables used in the medical field, the reference to patient monitoring systems may be interpreted broadly. Embodiments described herein can encompass those situations in which any system is used to data from a subject. Further, those of skill in the art will recognize that the present techniques are applicable to many different hardware configurations, software architectures, organizations, or processes.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the present techniques, including the best mode, and also to enable any person skilled in the art to practice the present techniques, including making and using any devices or systems and performing any incorporated methods. The patentable scope of the present techniques is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for ECG electrode and leadwire connection integrity detection, comprising:
   a plurality of electrodes, wherein a uniform spectral energy signal is to be injected into a subset of electrodes of the plurality of electrodes; and
   a computing device comprising a display, wherein the computing device is communicably coupled to the plurality of electrodes and is configured to:
   acquire input signals from an electrode;
   determine a frequency response from the electrode based on the input signal from the electrode; and
   determine impairments in the electrode and leadwire connection using the frequency response over a range of frequencies between a first and second frequency, wherein the first frequency is greater than or equal to 250 Hz, and the second frequency is less than 250 Hz.

2. The system of claim 1, wherein the subset of electrodes is a right leg (RL) electrode.

3. The system of claim 1, wherein the subset of electrodes includes a right arm electrode, a left arm electrode, a left leg electrode, a V1 electrode, a V2 electrode, a V3 electrode, a V4 electrode, a V5 electrode, and a V6 electrode.

4. The system of claim 1, wherein the frequency response is determined by calculating the Fast Fourier Transform (FFT) of the input signal appearing at the electrode.

5. The system of claim 1, wherein the frequency response is used to determine an impedance of the electrode, and the impedance of the electrode is used to determine a connection impairment of the electrode.

6. The system of claim 1, wherein the uniform spectral energy signal is a chirp signal.

7. The system of claim 1, wherein the uniform spectral energy signal is an impulse signal.

8. The system of claim 1, wherein the frequency response is used to detect and classify impairments in the electrode and leadwire connection.

9. The system of claim 1, wherein the computing device is a patient monitoring system.

10. An electrocardiograph (ECG) electrode and leadwire connection integrity detection system, comprising:
    a plurality of electrodes including a right leg electrode and a second electrode, the right leg electrode to be driven by a chirp signal and to be releasably attached to a patient, wherein an impedance and a frequency response between the second electrode and the right leg electrode is calculated over a range of frequencies between a first frequency and a second frequency, wherein the first frequency is greater than 250 Hz and the second frequency is less than 250 Hz, and the calculated impedance and the frequency response are used to determine a location of electrode connection impairment.

11. The ECG system of claim 10, wherein the chirp signal is a signal with a uniform spectral energy content.

12. The ECG system of claim 10, wherein the plurality of electrodes form a 12-lead ECG system.

13. The ECG system of claim 10, wherein the second electrode is any of a right arm electrode, a left arm electrode, a left leg electrode, or a chest electrode.

14. The ECG system of claim 10, wherein the calculated impedance is used to determine a location of a leadwire connection impairment.

15. A method for electrocardiograph (ECG) electrode and leadwire connection integrity detection, comprising:
    injecting a chirp signal into a neutral electrode;
    measuring an impedance at a plurality of electrodes across a range of frequencies from the chirp signal, wherein the range comprises a frequency greater than 250 Hz and a frequency less than 250 Hz;
    calculating an impedance and a frequency response of pairs of electrodes of the plurality of electrodes from the measured impedance across the range of frequencies; and
    determining an impairment location based on the calculated impedance and the frequency response.

16. The method of claim 15, wherein the neutral electrode is a right leg (RL) electrode of a 12-lead ECG system.

17. The method of claim 15, wherein the calculated impedance is used to determine an electrode impairment location or a leadwire impairment location.

18. The method of claim 15, comprising determining the impairment location prior to obtaining an electrocardiograph plot.

19. The method of claim 15, wherein the calculated impedance is used to classify an impairment.

* * * * *